(12) United States Patent
Wortmann et al.

(10) Patent No.: US 10,315,020 B2
(45) Date of Patent: Jun. 11, 2019

(54) DEVICE WITH TRANSDERMAL THERAPEUTIC SYSTEM, AND POSITIONING AID AND PENETRATION AID

(71) Applicant: LTS LOHMANN THERAPIE-SYSTEME AG, Andernach (DE)

(72) Inventors: Uwe Wortmann, Marburg (DE); Roman Hadaschik, Eisenach (DE); Michael Horstmann, Neuwied (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 333 days.

(21) Appl. No.: 14/998,302

(22) Filed: Dec. 24, 2015

(65) Prior Publication Data
US 2016/0166820 A1 Jun. 16, 2016

Related U.S. Application Data

(63) Continuation-in-part of application No. PCT/EP2014/063373, filed on Jun. 25, 2014.

(30) Foreign Application Priority Data

Jun. 25, 2013 (EP) .................................. 13173554

(51) Int. Cl.
*A61M 37/00* (2006.01)
*A61K 9/00* (2006.01)
*A61F 13/02* (2006.01)

(52) U.S. Cl.
CPC ..... *A61M 37/0015* (2013.01); *A61F 13/0236* (2013.01); *A61K 9/0021* (2013.01);
(Continued)

(58) Field of Classification Search
CPC .... A61M 37/0015; A61M 5/42; A61M 5/422; A61M 5/46; A61M 2037/0023;
(Continued)

(56) References Cited

U.S. PATENT DOCUMENTS

| 3,964,482 A | 6/1976 | Gertel et al. |
| 2002/0102292 A1 | 8/2002 | Cormier et al. |

(Continued)

FOREIGN PATENT DOCUMENTS

| WO | WO 2006/131931 A2 | 12/2006 |
| WO | WO 2012/075375 A1 | 6/2012 |

OTHER PUBLICATIONS

The English Translation of the International Preliminary Report on Patentability Including the Written Opinion of the International Searching Authority for the Corresponding International Patent Application (7 Pages); dated Jan. 7, 2016.
(Continued)

*Primary Examiner* — Bhisma Mehta
*Assistant Examiner* — James D Ponton
(74) *Attorney, Agent, or Firm* — Ronald S. Lombard

(57) ABSTRACT

A device with a positioning frame which can be adhered onto the skin and with a transdermal therapeutic system which can be inserted into a cut-out that passes through the positioning frame. The active substance dispensing outlet side of the inserted transdermal therapeutic system facing the skin. The device includes a tool unit which can be inserted into the cut-out of the positioning frame and centered in said cut-out in order to produce openings at least in the uppermost layer of the skin.

15 Claims, 3 Drawing Sheets

(52) U.S. Cl.
CPC ..... *A61M 37/00* (2013.01); *A61F 2013/0296* (2013.01); *A61M 2037/0023* (2013.01)

(58) Field of Classification Search
CPC ............ A61M 2037/0046; A61F 13/02; A61F 13/0236; A61F 13/024; A61F 13/0246; A61F 13/025; A61F 13/0253; A61F 13/0256; A61K 9/0021
See application file for complete search history.

(56) References Cited

U.S. PATENT DOCUMENTS

| | | | | |
|---|---|---|---|---|
| 2003/0225360 | A1* | 12/2003 | Eppstein | A61M 37/0015 604/19 |
| 2010/0286588 | A1* | 11/2010 | Bar-El | A61N 1/0424 604/20 |
| 2012/0310155 | A1* | 12/2012 | Heiser | A61M 5/425 604/82 |
| 2014/0207101 | A1* | 7/2014 | Moeckly | A61M 37/0015 604/506 |
| 2014/0236089 | A1* | 8/2014 | Brouwers | A61M 37/0015 604/173 |
| 2014/0243788 | A1* | 8/2014 | Cantor | A61M 37/0015 604/506 |

OTHER PUBLICATIONS

The International Search Report for the Corresponding International Patent Application—PCT/EP2014/063373, dated Jul. 15, 2014.

\* cited by examiner

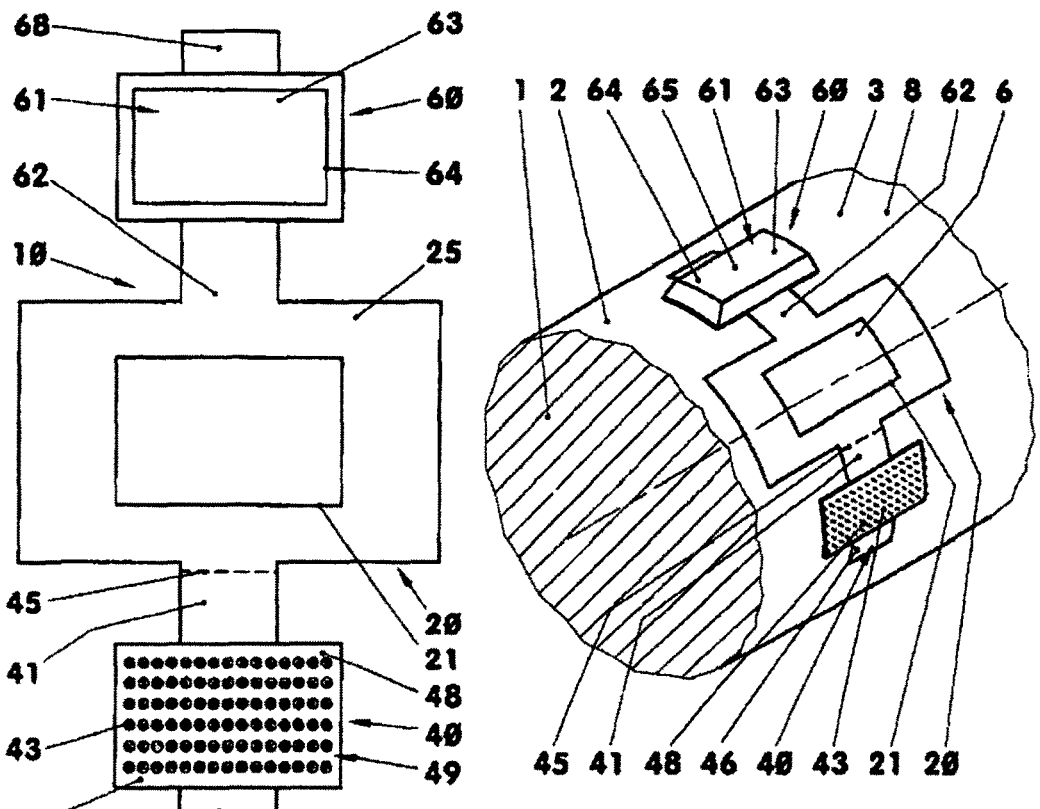
Fig. 1
Fig. 2
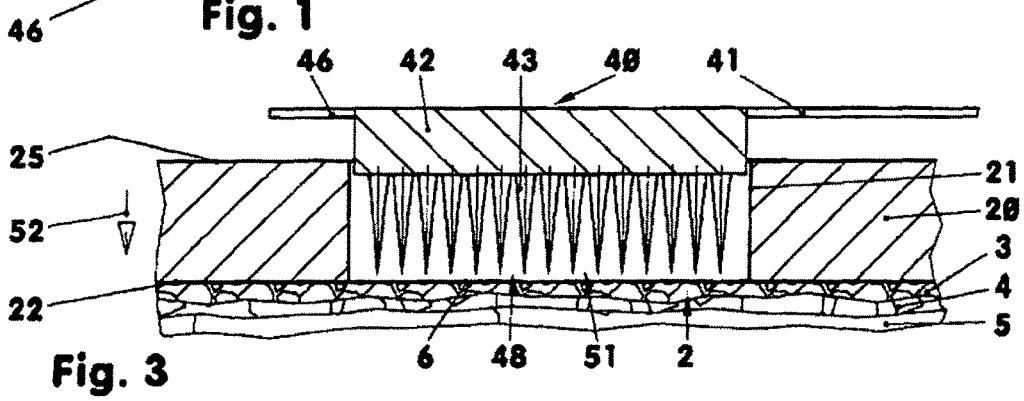
Fig. 3
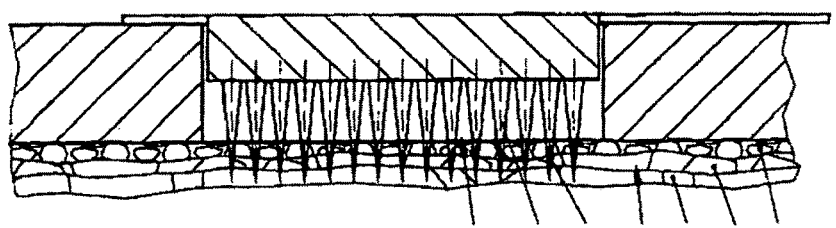
Fig. 4

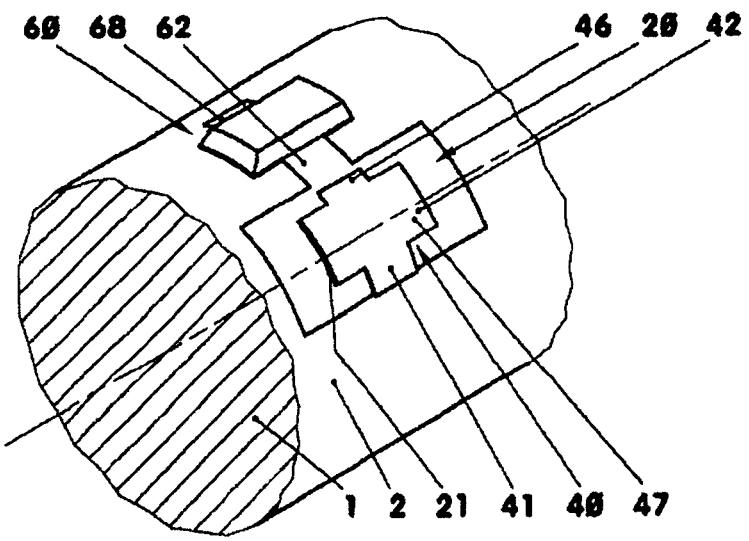
Fig. 5
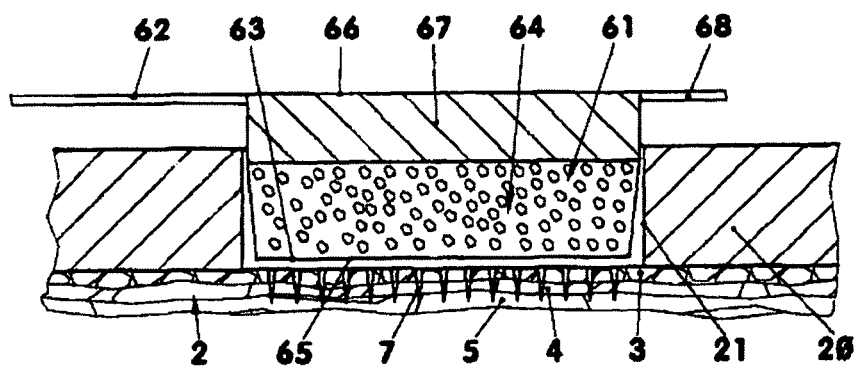
Fig. 6
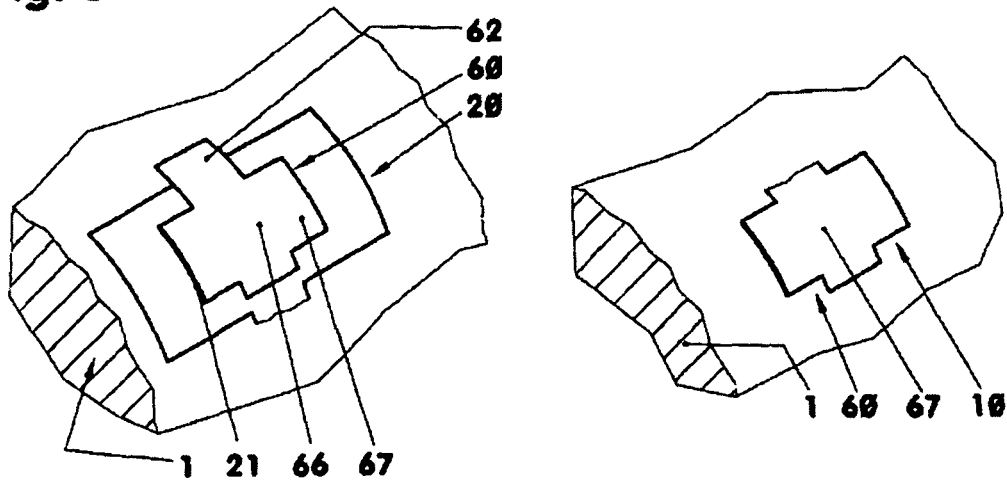
Fig. 7
Fig. 8

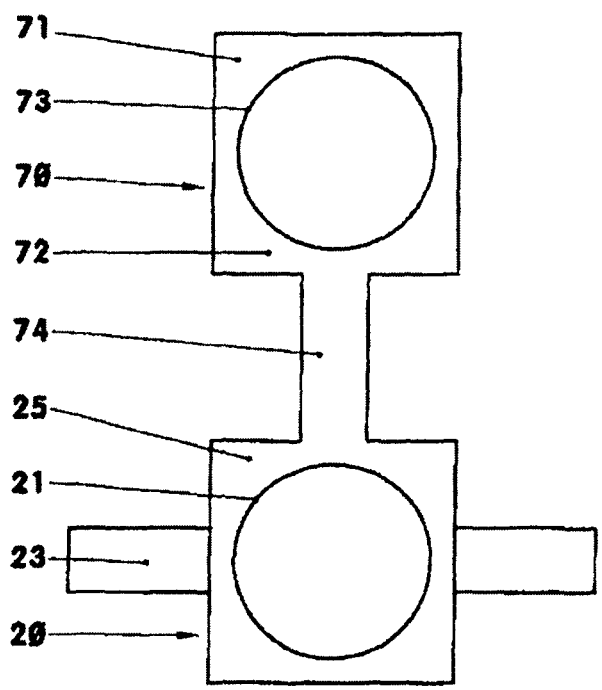
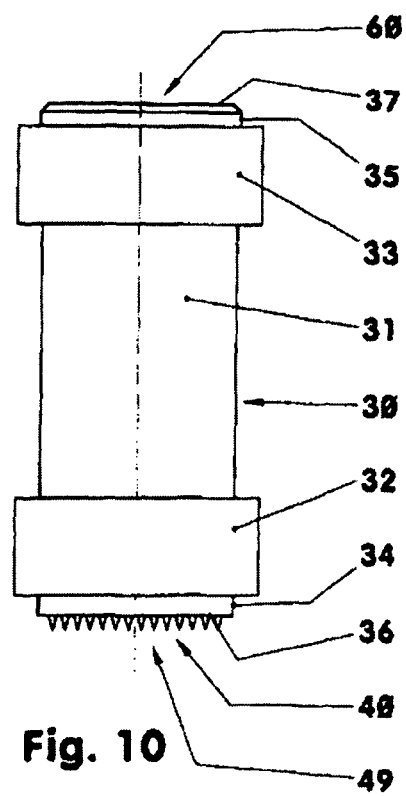
Fig. 9  Fig. 10
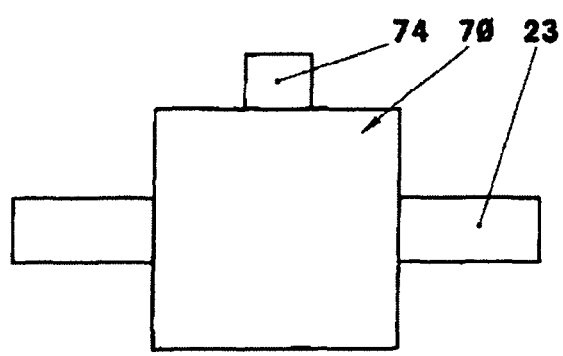
Fig. 11
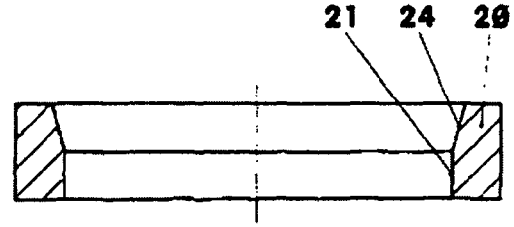
Fig. 12

DEVICE WITH TRANSDERMAL THERAPEUTIC SYSTEM, AND POSITIONING AID AND PENETRATION AID

CROSS-REFERENCE TO RELATED APPLICATIONS

This is a continuation-in-part application of pending international application PCT/EP2014/063373 filed Jun. 25, 2014, and claiming the priority of European application No. 13173554.0 filed Jun. 25, 2013. The said International application PCT/EP2014/063373 and European application No. 13173554.0 are both incorporated herein by reference in their entireties as though fully set forth.

BACKGROUND OF THE INVENTION

The invention relates to a device with a positioning frame which can be affixed to the skin and with a transdermal therapeutic system which can be inserted into a recess passing through the positioning frame, the active substance delivery side of the inserted transdermal therapeutic system facing the skin.

A device of this kind is known from WO 2006/131931 A2. The application of active substance can be impeded or prevented by the barrier properties of the skin.

The problem addressed by the present invention is that of improving the active substance transfer of the transdermal therapeutic system.

SUMMARY OF THE INVENTION

This problem is solved by the features of the claims, whereby the device comprises a tool unit which can be inserted into the recess of the positioning frame and centered in said recess in order to produce openings at least in the uppermost layer of the skin. The tool unit thus permits the perforation of the stratum corneum or is used to produce diffusion channels in the upper layer of skin.

BRIEF DESCRIPTION OF THE DRAWINGS

Further details of the invention will become clear from the claims and from the following descriptions of schematically depicted illustrative embodiments.

FIG. 1 shows the device with the positioning aid and penetration aid and with the transdermal therapeutic system;

FIG. 2 shows the device according to FIG. 1 when affixed to the skin;

FIG. 3 shows insertion of the tool unit;

FIG. 4 shows the device with tools pressed into the skin;

FIG. 5 shows the device according to FIG. 1 during the use of the perforation aid;

FIG. 6 shows insertion of the transdermal therapeutic system;

FIG. 7 shows the device according to FIG. 1 during the use of the transdermal therapeutic system;

FIG. 8 shows the device according to FIG. 4 after the positioning frame has been torn off;

FIG. 9 shows the closeable positioning frame;

FIG. 10 shows the stamp with the penetration aid and the transdermal therapeutic system;

FIG. 11 shows the closed positioning frame;

FIG. 12 shows the positioning frame with insertion taper.

DETAILED DESCRIPTION OF THE INVENTION

FIGS. 1-7 show a device (10) with a positioning frame (20), with an active substance unit (60) comprising a transdermal therapeutic system (61), and with a tool unit (40). FIG. 1 shows the device prior to use, wherein the devices for protection during storage and transportation have already been removed. In this plan view, the active substance unit (60) lies above and the tool unit (40) below the positioning frame (20). In this illustrative embodiment, the active substance unit (60) and the tool unit (40) are both connected to the positioning frame (20) in each case by means of a connecting tab (41, 62) configured, for example, as a film hinge.

In the plan view in FIG. 1, the positioning frame (20) is a rectangular frame of constant thickness. The thickness is, for example, less than three millimeters. The positioning frame (20) is made of an elastically deformable material. This can be a plastic, e.g. a polymer material. It can be produced from one or more components. In the case of a multi-component material, for example a two-component material, the area of the positioning frame (20) facing away from the observer of FIG. 1 can have a lower modulus of elasticity than the area of the positioning frame (20) facing toward the observer. Examples of materials that can be used for the positioning frame are polyethylene, silicone, TPE, pharmaceutical rubber, cellular rubber or cardboard, etc.

In the illustrative embodiment, the positioning frame (20) has a recess (21) which passes through it and which has a rectangular cross-sectional area. This recess (21) is, for example, symmetrical with respect to the vertical central longitudinal plane of the device (10) and symmetrical with respect to the vertical central transverse plane of the device (10). An adhesive layer is arranged (cf. FIG. 3) on the underside (22) of the positioning frame (20) facing away from the observer of FIG. 1.

In the plan view in FIG. 1, the active substance unit (60) likewise has a rectangular cross-sectional area. This cross-sectional area is slightly smaller than the cross-sectional area of the recess (21). For example, the length and the width of the cross-sectional area of the active substance unit (60) are each about a tenth of a millimeter smaller than the corresponding dimensions of the cross-sectional area of the recess (21). This difference can be between a hundredth of a millimeter and one millimeter. The surface of the active substance unit (60) facing toward the observer of FIG. 1 comprises the transdermal therapeutic system (61) with the active substance delivery side (63) of the active substance reservoir (64). An adhesive layer (65) is applied to what is here the upper face of the active substance delivery side (63) (cf. FIGS. 2 and 6). The rear face (66) of the active substance unit (60) forms a support plate (67).

The connecting tab (62) between the active substance unit (60) and the positioning frame (20) is produced from a bendable material. In the view in FIG. 1, it has a constant width. However, the connecting tab (62) can also have a constriction, a perforation, an indent, etc. This predetermined breaking point is arranged, for example, at a distance of five millimeters from the transdermal therapeutic system (61).

In the plan view shown in FIG. 1, the tool unit (40) has a rectangular cross-sectional area. This cross-sectional area is slightly smaller than the cross-sectional area of the recess (21). For example, the cross-sectional area of the tool unit (40) corresponds to the cross-sectional area of the active substance unit (60). In the view in FIG. 1, the tool unit (40) comprises a tool support (42) and a multiplicity of tools (43).

The tool support (42) has a plate-shaped construction. Its material has, for example, a higher modulus of elasticity than the material of the area of the positioning frame (20) facing away from the observer.

In the views in FIGS. 1-4, the tools (43) are needles (43) protruding from the tool support (42). In the illustrative embodiment, the tool unit (40) comprises 90 needles (43). The number of the needles (43) can be, for example, between ten and two thousand. In the illustrative embodiment, the multiplicity of needles (43) are arranged in a regular grid or an array. Circular, oval or polygonal arrangements, etc., are also conceivable.

The individual needles (43) protrude by the same amount from the tool support (42), such that their tips lie at least approximately in one plane. In the illustrative embodiment, the length by which the individual needles (43) protrude from the tool support (42) is shorter than the thickness of the positioning frame (20). For example, this length is 2.5 millimeters. The resulting possible depth of insertion of the needles (43) in the skin (2) is, for example, 0.4 to 0.8 mm. Other depths of insertion can be set by means of generally known modifications to the device. The needles (43) made of solid material are produced, for example, from an austenitic steel. The working space (51) of the tool unit (40) is thus arranged on the front face (48) of the tool unit (40). The cross-sectional area of the working space (51) is here delimited by the enveloping surface enclosing the tools (43). This cross-sectional area is smaller than the cross-sectional area of the recess (21) parallel thereto.

The tool unit (40) can also have a laser device, an ultrasound device or electrodes. These devices are conceivable as alternatives or additions to the needles (43).

The connecting tab (41), which connects the tool unit (40) to the positioning frame (20), is configured like the connecting tab (62) between the active substance unit (60) and the positioning frame (20). It has a perforation (45) which is arranged, for example, at a distance of 5 millimeters from the positioning frame (20). Instead of or in addition to the perforation (45), a constriction, an indent, etc., are also conceivable.

In the illustrative embodiment, the active substance unit (60) and the tool unit (40) both have an outwardly facing grip tab (46, 68). If appropriate, the positioning frame (20) can also have one or more grip tabs.

In the view in FIG. 2, the device (10) is applied to the skin (2) of the patient, e.g. to an arm (1). For this purpose, the positioning frame (20) is affixed to the skin (2) after a protective film has been peeled off. The positioning frame (20) is adapted to the shape of the arm (1), such that it is affixed completely on the arm (1). The positioning frame (20) surrounds a skin region (6). If appropriate, this skin region (6) is held taut by adherence of the positioning frame (20), which is deformation-resistant in regions.

The active substance unit (60) hangs on the connecting tab (62). The active substance delivery side (63) of the active substance reservoir (64) points in the direction away from the skin (2), i.e. upward in the illustrative embodiment. In the view in FIG. 2, the active substance unit (60) lies with its rear face (66) on the arm (1). If appropriate, when affixing the positioning frame (20), both the delivery side (63) of the active substance reservoir (64) and also the tool unit (40) can be protected by means of removable protective devices.

The tool unit (40) hangs on the connecting tab (41), with the tools (43) pointing in the direction away from the skin (2). For example, the tool support (42) lies with its rear face (47) on the skin (2) and conforms to the latter at least in some regions.

After the removal of the protective film, the tool unit (40) is pivoted about the film hinge of the connecting tab (41). In doing this, the tool unit (40) is held and guided by means of the grip tab (46). The tools (43) are inserted in insertion direction (52) into the recess (21) (cf. FIG. 3). The connecting tab (41) still connects the tool unit (40) to the positioning frame (20). If appropriate, the positioning frame (20) and/or the tool support (42) can have insertion tapers or other centering elements. These centering elements can be, for example, lugs, pins, holes, cutouts, etc., which can be arranged both on the positioning frame (20) and also on the tool unit (40). Upon further insertion, the tool support (42) is centered by means of the recess (21). At the start of the centering, the tools (43) are at a distance from the skin (2) (cf. FIG. 3). The working space (51) arranged on the front face (48) of the tool unit (40) is still not engaged by tools. The surface of the working space (51) projected onto the skin (2) is smaller than the cross-sectional area of the recess (21) surrounded by the positioning frame (20).

The tool unit (40) is pressed into the skin (2) (cf. FIG. 4). In doing so, the tools (43) penetrate the uppermost skin layers (3, 4, 5) and form openings (7) in these skin layers (3, 4, 5). In the view in FIG. 4, the two uppermost skin layers (3, 4) are penetrated completely. However, it is also conceivable that the needles (43) penetrate only the uppermost skin layer (3), i.e. the epidermis (3). While the tools (43) are pressed into the skin (2), the tool unit (40) is still centered by means of the positioning frame (20).

FIG. 5 shows the device (10) with the tool unit (40) pressed into the skin (2). The rear face (47) of the tool support (42) points outward, said tool support (42) protruding upward above the positioning frame (20). The tool unit (40) sits inside the recess (21) of the positioning frame (20). If appropriate, the pressing in of the tool unit (40) can be limited by means of a stop. For example, the connecting tab (41) and/or the grip tab (46) can form or comprise such a stop. The tool unit (40) can be shaped coaxially to the curvature of the skin (2) and/or of the positioning frame (20). The tool unit (40) and the positioning frame (20) are connected by means of the connecting tab (41). The grip tab (46) of the tool unit (40) points in the direction of the active substance unit (60) with the transdermal therapeutic system (61). The active substance unit (60) lies on the arm (1) in a manner unchanged from the view in FIG. 2.

To pull the tool unit (40) out of the recess (21), the user takes hold of the grip tab (46), e.g. with one hand, and pulls the tool unit (40) counter to the insertion direction (52). Thereafter, the tool unit (40) can be torn off along the perforation (45) and discarded.

After the removal of the protective film, the active substance unit (60) with the transdermal therapeutic system (61) is pivoted into the recess (21). To do so, the user takes hold of the grip tab (68), for example, and places the transdermal therapeutic system (61) into the recess (21) such that the support plate (67) is centered in the recess (21). In this state, the transdermal therapeutic system (61) does not yet touch the skin (2) of the patient (cf. FIG. 6). If appropriate, the support plate (67) can have centering bevels. The centering elements mentioned in connection with the tool unit (40) are also conceivable. The thickness of the active substance reservoir (64) of the transdermal therapeutic system (61) is smaller than the thickness of the positioning frame (20).

As the transdermal therapeutic system (61) is pressed in farther, the active substance delivery side (63) is pressed onto the exposed area (6) of the skin (2). At the same time, the transdermal therapeutic system (61) adheres to the skin (2). On being pressed in farther, the active substance unit (60) is further centered by means of the recess (21). If appropriate, the pressing-in stroke is limited by means of a stop. The connecting tab (62) and/or the grip tab (68) can form or comprise such a stop.

FIG. 7 shows the device (10) with the transdermal therapeutic system (61) inserted into the recess (21) and pressed onto the skin (2). The support plate (67) of the active substance unit (60) protrudes slightly above the positioning frame (20). The active substance from the active substance container (64) is delivered from the delivery side (63) into the skin (2). In this process, the active substance passes through the openings (7), generated by means of the penetration aid (40), into the skin layers (4, 5) below the stratum corneum (3). This results in an effective subcutaneous introduction of active substance.

After the transdermal therapeutic system (61) has been applied and affixed, the positioning frame (20) can be removed. For this purpose, it can be grasped at a corner or via a grip piece, for example, and pulled off the skin (2). The transdermal therapeutic system (61) here remains on the skin (2). When the positioning frame (20) is pulled off, the connecting tab (62) is, for example, torn off at a perforation. The positioning frame (20) can now be discarded. FIG. 8 shows the arm (1) of the patient with the device (10) reduced to the active substance unit (60). By means of the transdermal therapeutic system (61) positioned with the aid of the positioning frame (20), active substance continues to be introduced into the skin (2) of the patient. The position of the transdermal therapeutic system (61) can additionally be secured by means of a plaster. If appropriate, when using such a plaster, it is possible to dispense with the adhesive layer (65) on the active substance delivery side (63).

In the case of perforation of the skin (2) by means of laser or ultrasound, a centering of the tool unit (40) in the positioning frame (21) likewise takes place. The centering of the active substance unit (60) and the introduction of the active substance take place as described above.

FIGS. 9-11 show a further embodiment of the device (10). FIG. 9 shows a positioning frame (20) with a cover (70). This positioning frame (20), with a square base surface for example, has a recess (21) with a circular cross-sectional area. Two plasters (23) are arranged laterally on the positioning frame (20) and are used to affix the positioning frame (20) to the skin (2) of the patient. The material and the material thickness of the positioning frame (20) correspond to the data cited in connection with the first illustrative embodiment.

In this illustrative embodiment, the cover (70) has a square base surface. The front face (71) of the support plate (72) of the cover (70) facing the observer of FIG. 9 carries a centrally arranged cylindrical or frustoconical centering projection (73). The maximum cross-sectional area of the centering projection (73) is smaller than the cross-sectional area of the recess (21). The difference in size between the centering projection (73) and the recess (21) can correspond to the size differences cited in connection with the first illustrative embodiment.

The cover (70) is connected to the positioning frame (20) by means of a bendable connecting tab (74). This connecting tab (74) is configured like the connecting tabs (41, 62) described in connection with the first illustrative embodiment.

FIG. 10 shows a stamp (30) as part of the device (10). This stamp (30) has, for example, a cylindrical main body (31). Reinforcing rings (32, 33) surrounding the main cylinder (31) are arranged at each end. The respective reinforcing ring (32, 33) is set apart from the respective end face (36, 37) of the main cylinder (31) by an insertion area (34, 35). The end face (36) at the bottom in FIG. 10 carries a tool unit (40). The latter comprises a multiplicity of needles (43). The number and the design of the needles (43) correspond to the number and the design of the needles (43) described in connection with the first illustrative embodiment. Instead of a needle array (49), the tool unit (40) can comprise a laser assembly, an ultrasound assembly, electrodes, etc. The tool unit (40) can then be arranged on or in the stamp (30). In the initial state, the tool unit (40) is protected by means of a protective film, for example.

The end face (37) of the stamp (30) remote from the tool unit (40) carries an active substance unit (60) with a transdermal therapeutic system (61). In this illustrative embodiment, the active substance delivery side (63) of the transdermal therapeutic system (61) can be designed with or without an adhesive layer.

After the positioning frame (20) has been affixed to the skin (2), the stamp (30) is inserted, with the tool unit (40) to the front, into the recess (21) of the positioning frame (20). In doing so, the insertion area (34) is centered in the recess (21) of the positioning frame (20). The centering can be such as has been described in connection with the first illustrative embodiment. In this illustrative embodiment too, as the pressing in continues, the tools (43) of the tool unit (40) penetrate at least the uppermost layer (3) of the skin (2). The skin (2) is perforated. The tool unit (40) can, for example, be pressed onto the skin (2) until the reinforcing ring (32) lies on the positioning frame (20). Here, the reinforcing ring (32) forms, together with the positioning frame (20), a limit stop for the tool unit (40).

The stamp (30) is now withdrawn again. If appropriate, the tool unit (40) can be provided with a protective cap. Next, the stamp (40) is inserted with the other end face (37), on which the transdermal therapeutic system (61) is arranged, into the recess (21) of the positioning frame (20). In doing so, the insertion area (35) is placed and centered in the recess (21) of the positioning frame (20). On being pushed in farther, the transdermal therapeutic system (61) touches the exposed area (6) of the skin (2) via its active substance delivery side (63). The continued pressing in of the stamp (30) causes the active substance to be discharged from the active substance container (64) through the skin openings (7) and into the skin layers (4, 5) below the stratum corneum (3). The pressing in continues until the reinforcing ring (33) lies on the positioning frame (20) and, if appropriate, has remained there for a predetermined period of time. The limit stop prevents further pushing in of the transdermal therapeutic system (61) and thus prevents uncontrolled delivery of active substance.

After the removal of the stamp (30), the positioning frame can be closed by means of the cover (70) (cf. FIG. 11). The cover is here centered in the recess (21) by means of the centering projection (73). If appropriate, the cover can adhere to the skin (2). Depending on the structure of the positioning frame (20), the latter can now be removed from the skin (2). The adhesive for affixing the positioning frame (20) to the skin (2) can have a different formulation than the adhesive for affixing the transdermal therapeutic system (61) to the skin (2). For example, the adhesive of the positioning frame (20) requires less force to be applied to release the positioning frame (20) from the skin (2) than does the adhesive of the transdermal therapeutic system (61).

The stamp (30) can also be designed in such a way that the transdermal therapeutic system (61) is deposited in the recess (21) by means of the stamp (30). The use of another tool for placing the transdermal therapeutic system (61) in the recess (21) is also conceivable. In all cases, after insertion, the active substance delivery side (63) of the transdermal therapeutic system (61) points in the direction of the skin (2).

After the transdermal therapeutic system (61) has been applied, the cover (70) is centered on the recess (21) and closed. In this case too, the discharge of the active substance from the active substance container (64) takes place via the openings (7) introduced into the skin (2).

The transdermal therapeutic system (61) can also be integrated in the cover (70). After the perforation of the skin (2) by means of the tool unit (40), the cover (70) is pivoted into the recess (21), as has been described in connection with the first illustrative embodiment.

FIG. 12 shows a positioning frame (20) whose recess (21) has an insertion taper (24). The imaginary cone tip lies below the skin surface (8) (cf. FIG. 2). The apex angle of the insertion taper (24) is 30 degrees, for example. This angle can be between 5 degrees and 45 degrees. The length of this chamfer is shorter than or equal to half the length of the recess (21) perpendicular to the skin (2). In the case of a rectangular cross-sectional area of the recess (21), insertion bevels are formed instead of an insertion taper (24). The inserting and centering elements can also be arranged on the top face (25) of the positioning frame (20) directed away from the skin (2).

Of course, it is also conceivable for the various embodiments mentioned to be combined with one another.

LIST OF REFERENCE SIGNS

1 arm
2 skin
3 epidermis, stratum corneum, uppermost layer of skin
4 second layer of skin
5 third layer of skin
6 skin region, exposed area
7 openings
8 skin surface
10 device
20 positioning frame
21 recess
22 underside of (20)
23 plaster
24 insertion taper, centering element
25 top face of (20)
30 stamp
31 main body, main cylinder
32 reinforcing ring, on tool side
33 reinforcing ring, on active substance side
34 insertion area, on tool side
35 insertion area, on active substance side
36 end face, on tool side
37 end face, on active substance side
40 tool unit, penetration aid
41 connecting tab
42 tool support
43 tools, needles
45 perforation
46 grip tab
47 rear face
48 front face
49 needle array
51 working space
52 insertion direction
60 active substance unit
61 transdermal therapeutic system
62 connecting tab
63 delivery side, active substance delivery side
64 active substance reservoir, active substance container
65 adhesive layer
66 rear face
67 support plate
68 grip tab
70 cover
71 front face
72 support plate
73 centering projection
74 connecting tab

What is claimed is:

1. A device (10) comprising:
a positioning frame (20) which can be affixed to skin (2) of a patient and including an attached active substance unit (60) including a transdermal therapeutic system (61) including an
active substance container (64) configured to be insertable into a recess (21) passing through the positioning frame (20)
an active substance delivery side (63) of the insertable active substance container (64) facing the skin (2) after insertion in the positioning frame (20),
the positioning frame (20) including a first connecting tab (62) in operative attachment arrangement with the active substance unit (60),
the positioning frame (20) including an attached tool unit (40) comprising a tool support (42) carrying a multiplicity of tools (43),
the positioning frame (20) including a second connecting tab (41) in operative attachment arrangement with the tool unit (40),
the tool unit (40) configured to be insertable into the recess (21) of the positioning frame (20) and to be centered in said recess in order to produce openings (7) at least in an uppermost layer (3) of the skin (2),
wherein:
the tools (43) are configured as needles,
the needles (43) are held in the tool support (42),
the needles (43) have a length protruding from the tool support (42) which is shorter than a thickness of the positioning frame (20), and,
the second connecting tab (41) is configured to act as a limit stop for limiting a depth of insertion of the multiplicity of needles (43) into the skin (2).

2. The device (10) as claimed in claim 1, characterized in that the active substance delivery side (63) of the insertable active substance container (64) carries an adhesive layer (65) for adhering to the skin (2).

3. The device as claimed in claim 2, characterized in that the active substance container (64) contains an active substance of the transdermal therapeutic system (61), the active substance container (64) having a thickness less than a thickness of the positioning frame (20).

4. The device (10) as claimed in claim 1, characterized in that the first connecting tab (62) and the second connecting tab (41) are configured to be bendable.

5. The device (10) as claimed in claim 4, characterized in that the active substance unit (60) has a support plate (67) facing away from the transdermal therapeutic system (61).

6. The device (10) as claimed in claim 1, characterized in that the recess (21) has an insertion taper (24) or insertion bevels.

7. The device (10) as claimed in claim 1, characterized in that the first connecting tab (62) and the second connecting tab (41) are configured to be breakable.

8. The device (10) of claim 1, further comprising a first grip tab (46) in operative attachment arrangement with the tool unit (40), whereby the tool unit (40) may be guided into the recess (21).

9. The device (10) of claim 8, further comprising a second grip tab (68) in operative attachment arrangement with the active substance unit (60), whereby the active substance unit (60) may be guided into the recess (21).

10. The device (10) of claim 1, wherein the first connecting tab (62) is configured to act as a limit stop for limiting a pressing-in stroke of the active substance unit (60) within the recess (21).

11. A device (10) comprising:
a positioning frame (20) configured to be affixed to skin (2) of a patient,
a stamp (30) including a main body (31) having a first end face (36) carrying a tool unit (40) and a second end face (37) remote from the tool unit (40) carrying an active substance unit (60) including a transdermal therapeutic system (61) including an active substance container (64) configured to be insertable into a recess (21) passing through the positioning frame (20),
an active substance delivery side (63) of the insertable active substance container (64) facing the skin (2) after insertion in the positioning frame (20),
the recess (21) of the positioning frame (20) configured to alternately receive the first end face (36) of the stamp (30) carrying the tool unit (40) and subsequently configured to receive the second end face (37) of the stamp (30) carrying the active substance unit (60), and
the tool unit (40) configured to be insertable into the recess (21) of the positioning frame (20) and centered in said recess in order to produce openings (7) at least in an uppermost layer (3) of the skin (2).

12. The device of claim 11, wherein the main body (31) of the stamp (30) includes a first reinforcing ring (32) surrounding the main body (31) and separated from the first end face (36) by an insertion area (34), the tool unit (40) carries a multiplicity of needles (43), each needle of the multiplicity of needles protruding by a same amount from the first end face (36), the first reinforcing ring (32) together with the positioning frame (20) configured as a first limit stop for the tool unit (40) for limiting a depth of insertion into the skin (2) the multiplicity of needles (43) can be inserted.

13. The device of claim 12, wherein the main body (31) of the stamp (30) includes a second reinforcing ring (33) surrounding the main body (31) and separated from the second end face (37) by an insertion area (35), the insertion area (35) is configured to be insertable in the recess (21), the second reinforcing ring (33) configured as a second limit stop to contact the positioning frame (20) for preventing further pushing in of the transdermal therapeutic system (61), whereby uncontrolled delivery of the active substance is prevented.

14. The device as claimed in claim 12, characterized in that a length that the multiplicity of needles (43) protrude from the end face (36) is shorter than a thickness of the positioning frame (20).

15. The device (10) of claim 11, further comprising a cover (70) including a support plate (72) that is connected to the positioning frame (20) by a bendable connecting tab (74), the support plate (72) including a front face (71) having a centrally arranged cylindrical or frustoconical centering projection (73) for aligning with the recess (21) for closing the positioning frame (20).

* * * * *